(12) United States Patent
Mackay

(10) Patent No.: US 7,004,939 B2
(45) Date of Patent: Feb. 28, 2006

(54) ELECTROSURGICAL APPARATUS

(76) Inventor: Dale Victor Mackay, 29 Amess Street, Carlton North, Victoria (AU) 3054

( * ) Notice: Subject to any disclaimer, the term of this patent is extended or adjusted under 35 U.S.C. 154(b) by 0 days.

(21) Appl. No.: 10/233,713

(22) Filed: Sep. 3, 2002

(65) Prior Publication Data

US 2004/0044342 A1 Mar. 4, 2004

(51) Int. Cl.
A61B 18/18 (2006.01)
(52) U.S. Cl. .............................. 606/40; 606/49; 606/41
(58) Field of Classification Search ............ 606/37–41, 606/45, 46, 48–50
See application file for complete search history.

(56) References Cited

U.S. PATENT DOCUMENTS

| 2,708,933 | A | | 5/1955 | August |
| 2,828,747 | A | | 4/1958 | August |
| 4,040,426 | A | | 8/1977 | Morrison, Jr. |
| 4,060,088 | A | | 11/1977 | Morrison, Jr. et al. |
| 4,781,175 | A | | 11/1988 | McGreevy et al. |
| 4,901,719 | A | * | 2/1990 | Trenconsky et al. .......... 606/49 |
| 4,927,420 | A | | 5/1990 | Newkirk et al. |
| 5,088,997 | A | * | 2/1992 | Delahuerga et al. .......... 606/42 |
| 5,098,430 | A | | 3/1992 | Fleenor |
| 5,186,714 | A | * | 2/1993 | Boudreault et al. ........... 604/21 |
| 5,720,745 | A | * | 2/1998 | Farin et al. .................... 606/49 |
| 6,149,648 | A | * | 11/2000 | Cosmescu ..................... 606/42 |
| 6,602,249 | B1 | * | 8/2003 | Stoddard et al. .............. 606/45 |

FOREIGN PATENT DOCUMENTS

AU 200071586 A1 * 5/2002

OTHER PUBLICATIONS

Invention Disclosure Form dated Nov. 13, 2000.

* cited by examiner

Primary Examiner—Michael Peffley
(74) Attorney, Agent, or Firm—Patent Law Offices of Rick Martin, PC

(57) ABSTRACT

An apparatus for performing electrosurgery that employs a tungsten electrode that enables the flow of an inert gas (argon or helium) to flow and shroud the electrode during its use. The electrode may have a variety of tip configurations for different and varied surgical applications.

6 Claims, 3 Drawing Sheets

ELECTROSURGICAL APPARATUS

CROSS-REFERENCE TO RELATED APPLICATION

This application is a non-provisional application claiming no benefit of an earlier filed application.

STATEMENT OF GOVERNMENT INTEREST

The subject matter of this application was not carried out under contract with the government of the United States.

FIELD OF THE INVENTION

This application relates to a device for performing electrosurgical procedures such as cutting, dissection, and fulguration. More specifically it relates to monopolar electrosurgical devices

BACKGROUND OF THE INVENTION

Electrosurgery is the use of an electric current to effect tissues in surgical procedures. Electrosurgery can be practiced using bipolar or monopolar modality. In a bipolar mode, electrosurgical equipment passes current between two conductive parts of the instrument, resulting in an arc. Tissue positioned between the conductive parts is vaporized and the wound site is cauterized by the heat generated in the electrical discharge. In monopolar modality, the patient is incorporated into an electric circuit, such that the patient supplies a ground contact to an instrument that is in ohmic contact with a high energy electron source (the electrosurgical generator). Discharge between the electrosurgical instrument and the patient produces the electrosurgical effect.

The basic procedures available using monopolar electrosurgical equipment are cutting, fulguration, desiccation, and coagulation. Cutting occurs when a surgeon selects voltage and current settings such that cells in the subject tissues are vaporized. Because of the heat involved, electrosurgical cuts are usually accompanied by hemostatis in the surgical wound, however, it is possible to select power settings in which a purely surgical cut is effected by an electrosurgical scalpel.

Fulguration, a combination of tissue dehydration and charring, occurs at high voltage settings and is used generally to seal tissue over a wide area. To reduce tissue destruction, fulguration is generally preformed with a modulated power source, such that the power is only applied to the electrosurgical device in short "bursts". The power can be adjusted to give a range of effects which yield a wound ranging from dehydrated tissue covered with a light eschar to tissues layered in charred material over eschar over dehydrated tissues. Cutting and fulguration are accomplished by discharge from the electrode to the tissue (no tissue contact with the electrode).

Desiccation is accomplished by directly contacting cellular tissue with a low voltage electrosurgical current. This direct contact generates sufficient heat to dehydrate the upper layer of cells (desiccation) but does not generate sufficient heat to vaporize or rupture the cellular structure.

The quality of the wound produced by electrosurgical devices, thus the degree to which hemostatis can be achieved and the level of trauma imparted to tissues during the procedure, and subsequently, the ease of healing of the surgical wound after the procedure can be controlled by tailoring the quality of the electrosurgical discharge during the procedure. One method of moderating the destructive effects of electrical discharge has been accomplished through the introduction of a gas stream into the discharge path of an electrosurgical apparatus. In gas enhanced electrosurgery, an inert gas which is easily ionized, such as argon or helium, is introduced into the surgical site. The gas is used both to moderate the discharge, making for a more uniform arc to the surgical site, and to "blanket" the surgical site, such that charring (burning) of the tissue is suppressed. It is thought that easily ionizable gasses also reduce heating of the electrode, and thus suppress electrode destruction and material transfer from the electrode to the tissue.

Thus, U.S. Pat. No. 2,618,267 to Hanriot discloses a control system for controlling a gas blanket directed at blanketing an electrosurgical instrument. This patent does not teach management of the gas stream regarding contact of the instrument with the surgical site.

U.S. Pat. Nos. 2,708,933 and 2,828,747 to August disclose electrosurgical instruments utilizing an argon shroud about the cutting element of the instrument, the purpose of which is to prevent contacting explosive anesthesia vapors with electrical discharge. These patents do not teach the management of inert gas pressure during contact of the instrument with tissues in the surgical site.

In U.S. Pat. No. 4,040,426 to Morrison, an electrosurgical device is described in which argon or helium is flowed through a tube arranged coaxially about an electrode that protrudes from the end of said tube. The '426 patent teaches that electrostatic charge is built up on the surrounding tube by the flow of gas through the tube, which participates in corona discharge between the electrode and the surrounding tube. This discharge produces a stream of ionized gas that participates in facilitating discharge between the tissue at the surgical site and an electrode (when this assembly is employed in an electrosurgical device) without contact between the tissue and the electrode. The '426 patent teaches that discharge occurs along the length of the coaxial tube that is proximate to the electrode while gas is flowing and the electrode is energized. The '426 patent teaches that the arrangement disclosed dissipates power from an electrosurgical generator along the gas tube/electrode pathway rather than through the electrode/tissue gap of conventional electrosurgical arrangements.

U.S. Pat. No. 4,060,088 to Morrison et al. teaches the use of a hollow electrode in an electrosurgical apparatus, wherein an inert gas is passed through the electrode, providing a low resistance discharge pathway to the surgical site. Additionally, the '088 patent teaches the use of a hollow electrode coaxially placed within a gas conduit. In such an arrangement, a columnated beam of ionized gas can be directed at a surgical site when such a construct is employed in an electrosurgical apparatus. Such a beam was disclosed to be effective in controlled fulguration procedures leading to superior condition of the tissues in the surgical site over electrosurgical fulguration methods not employing an inert gas in the electrical discharge. The '088 patent teaches that there is no functional difference between an electrode protruding from the jacket conducting gas past the electrode and one contained wholly within such a jacket in the effectiveness of the device in fulguration procedures.

U.S. Pat. No. 4,781,175 to McGreevy et al. discloses an electrosurgical apparatus consisting of a pencil unit which embodies an electrosurgical instrument, a gas delivery unit, and an electric power delivery unit. The '175 teaches, with regard to electrical discharge from the electrosurgical instrument, that a gas jet can be interfaced with the electrosurgical instrument which will facilitate a more even and stable discharge between the apparatus and the surgical wound and clear fluids from the surgical site during cutting procedures. The '175 patent discloses a surgical pencil for carrying out surgical procedures having an inert gas dispensing nozzle, and in which the electrode of the device is contained within that nozzle. No teaching is imparted regarding the shape or material of the electrode used in the disclosed electrosurgical pencil.

U.S. Pat. No. 4,927,420 to Newkirk et al. discloses how to make and use a refractory alloy electrode in an electrosurgical instrument. The disclosed refractory metal electrode is characterized by its resistance to thermal degradation of its finely formed end. The '420 patent discloses that by fitting electrosurgical instruments with electrodes having tips of small cross-sectional area, tissue damage common with instruments employing large cross-sectional area electrodes is reduced. The '420 patent also teaches how to make electrodes with the subject small cross-sectional area tip from refractory metal wire. The '420 patent discloses that the subject electrodes may be employed with mono- or bipolar electrosurgical systems, but does not teach or disclose use of the electrodes with inert gas blanketing U.S. Pat. No. 5,098,430 to Fleenor discloses an electrosurgical pencil that has a retractable nozzle enclosing an electrode which is retractable at the surgeons will during a procedure. Using this device, an electrosurgical implement can be operated in both gas enhanced non-contact mode or non-gas enhanced direct contact mode. The '430 patent teaches that in ordinary equipment, the instrument arrangement required for gas enhanced fulguration is not compatible with that required in an instrument intended for direct contact electrosurgical dissection. The requirements for a laminar flow shield completely isolating the electrode of the instrument precludes using such an implement because the electrode can not be contacted to the tissue when shielded for gas enhanced operation. The '430 patent discloses and instrument that can be used in conventional (non-gas enhanced) direct contact electrosurgical procedures such as cutting, and in gas enhanced (non-contact) fulguration of tissues, permitting a surgeon to engage in a full range of electosurgical techniques with one implement. The '430 patent additionally discloses a control mechanism mounted on the surgical pencil affording a surgeon operation of the electrosurgical apparatus and the retractable nozzle using the same hand controlling the pencil during a surgical procedure.

Although prior art has taught a number of methods by which electrosurgical discharge may be utilized in delicate surgical work, and has taught gas enhancement of tissue fulguration as a method of improving surgical result, some problems still remain. In general electrosurgical procedures, contact with tissue usually results in tissue adhering to the electrode. The adhered tissue can rip open the surgical wound, complicating the outcome of the surgery. To counteract this tendency, fully coated prior art electrodes have been produced, however these devices require higher voltages to overcome the impedance and resistance offered by the coatings. These higher voltages can exacerbate discharge instability, concentrating the energy of the electrosurgical instrument in very localized areas. This concentrated discharge leads to uneven eschar and often to excessive tissue necrosis in the surgical wound. In endoscopic procedures, electrode insulation can serve to facilitate the formation of an unintended capacitance in the electrosurgical instrument which discharges in an unintended manner through the patient which can result in unintended tissue damage.

In a gas enhanced mode, accidental contact of the electrosurgical instrument with the tissues in the surgical site can lead to the formation of a gas embolism in the patient, which can lead to surgical complication or death of the patient. The present invention addresses these problems associated with gas enhanced, monopolar electrosurgical instruments.

SUMMARY OF THE INVENTION

The present invention incorporates a refractory metal electrode of small tip diameter and an inert gas delivery system that incorporates a means of managing gas pressure during direct tissue/instrument contact into an electrosurgical instrument that may be used without adaptation in both contact and non-contact electrosurgical procedures. One aspect of the present invention is an improved surgical outcome in various electrosurgical procedure using voltages comparable or lower than conventional electrosurgical instruments without danger of accidental inducement of embolism in tissue within the surgical area.

Other aspects of this invention will appear from the following description and appended claims, reference being made to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF DRAWINGS

Figure 1:
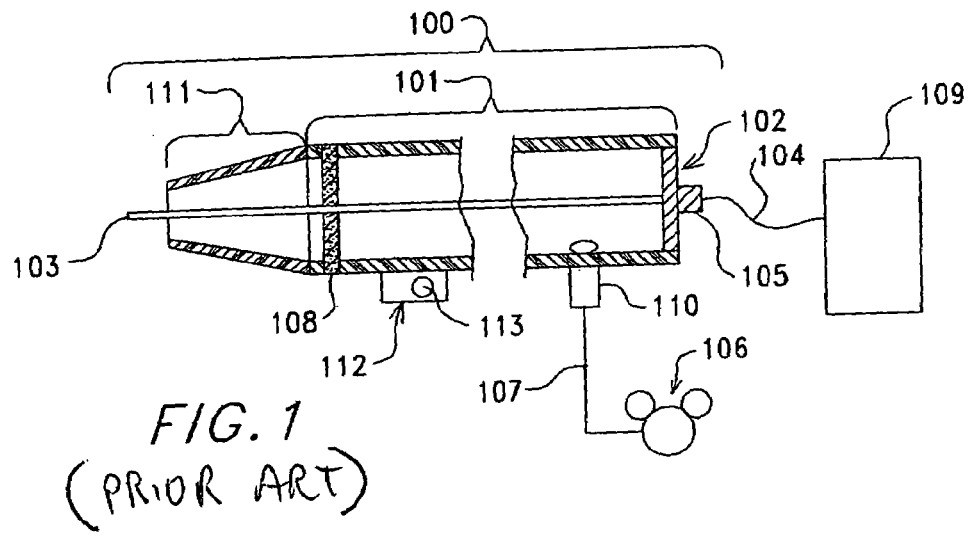
FIG. 1: Cutaway Plan View of a Prior Art Surgical Pen.

With reference to FIG. 1, the conventional instrument for electrosurgery comprises a handle 101 by which the surgeon manipulates the instrument, an electrode holding device 102 on or within the handle which rigidly secures the electrode 103 to handle 101, and a means for attaching a source of radio frequency (rf) energy 109 to electrode 103, generally a cable 104 and plug 105 arrangement whereby the instrument may be removably connected to the rf source. In some of the prior art instruments, the handle is also fitted with a means for connecting the instrument to a gas supply 106. Typically, a flexible conduit 107 is connected to handle 101 by connector means 110. Connector means 110 and hollow handle 101 conduct the gas to electrode 103, plenum 108 and nozzle 111 whereby the gas is distributed about the electrode. In prior art devices, nozzle 111 extends beyond electrode 103, providing a columnated source of gas for non-contact electrosurgical procedures. Prior art devices intended to be used in procedures requiring electrode contact with the tissue employ a gas conduit that terminates in an electrode-mounting device, leaving the electrode exposed with a gas stream emerging from the handle and blanketing the surgical site.

The entire assembled instrument 100 is often referred to in the prior art as an electrosurgical pencil, even though it may be fitted with a variety of electrodes having various shapes or end configurations such that it may serve as a scalpel, needle, hook, or other specialized instrument. In some prior art instruments, a pod 112 containing one or more switches 113 have also been mounted on handle 101 to provide means of controlling application of rf energy to electrode 103 and initiate gas flow through conduit 107.

Figure 2:
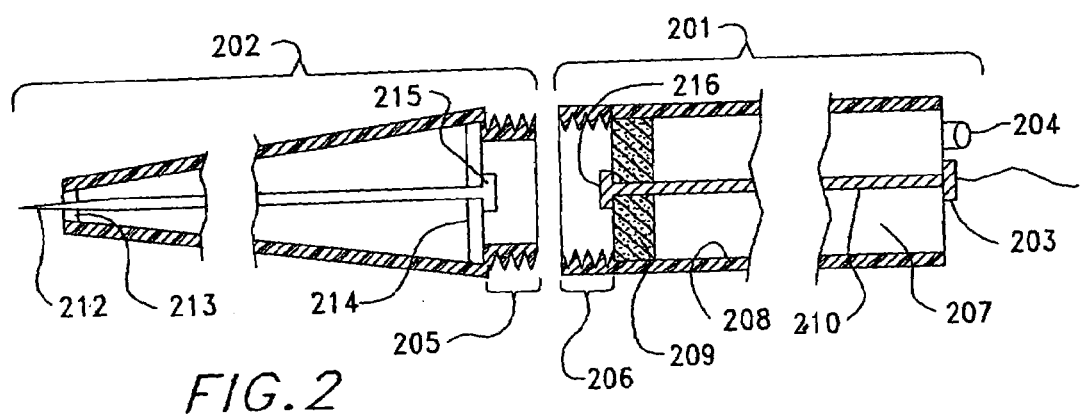
FIG. 2: Cutaway Plan View of a Surgical Pen According to the Present Invention.

With reference to FIG. 2, the present invention utilizes handle 201 which is a hollow tube having provisions on one end to receive nozzle assembly 202. Handle 201 of the present invention, like the handle of the prior art devices, serves as a means of permitting the surgeon to manipulate the assembled instrument during a procedure as well as bearing mounting device 203 for rf power cables and 204 for gas supply conduits.

Nozzle assembly 202, disclosed in detail below, contains electrode 212 mounted within it. Additionally, also mounted within nozzle assembly 202 are baffle plate 213 and support plate 214. In use, nozzle assembly 202 is secured to handle 201. Any number of means such as is well known in the art may be used to attach nozzle assembly 202 to handle 201. One such example utilizes a spring loaded sleeve and pin type connector, commonly called a bayonet mount (not illustrated). Another method may employ a close tolerance collar and stem assembly utilizing a snap ring or locking collar to hold it into place, such as will be familiar to those skilled in the art. Additionally, a screw-in type fitting (illustrated in FIG. 2) consisting of outside threaded portion 205 and inside threaded portion 206, which is preferred in the present invention because it mounts securely and is easily exchanged.

One requirement of a connector utilized to connect nozzle assembly 202 to handle 201 is that it rigidly affixes the two members such that motion imparted to the handle is communicated to the nozzle assembly without distortion due to flexure or instability in the connector. A second requirement of the connector is that it provide reliable electrical contact between electrode end contact 215 and handle feed-through contact 216 during manipulation of the instrument in a surgical procedure.

In addition to serving as a handle for manipulating the electrode and as a mounting point for gas conduits and connectors to facilitate connection of a source of rf energy to the electrode, the handle may be hollow, forming a conduit through which gas and rf current is passed. Thus, with further reference to FIG. 2, handle 201 is conveniently bored through to form chamber 207. Conduit 204, which is fitted with a connector suitable for attaching a gas line to the handle and chamber 207 form a means of conducting gas into nozzle assembly 202 which does not impede gripping or manipulation of the instrument, and so is preferred. External conduits fastened to or molded into handle 201 could also be used with equal effectiveness. Additionally, a pod (not shown) may be removably or permanently mounted on handle 201 to provide a convenient place for mounting switches by which finger motion could be used to initiate inert gas flow and control the application of rf power to electrode Support plate 209 is attached within the bore of chamber 207. Support plate 209 is perforated to permit gas introduced into conduit 204 to flow past it. Alternatively, support plate 209 could be made of rigid porous material such as a course metal or plastic frit of the type available from Mott Metal corporation. If fritted material is chosen for support plate 209, it must be of sufficient thickness to maintain feed-through conductor 210 in place under contact load from nozzle assembly 202 when contact faces 215 and 216 are brought together during assembly of the instrument and still permit gas to flow past the support plate.

In alternative embodiments, feed through conductor 210 could be a conductive coating placed on inner wall 208 of hollow handle 201 or a conductive tube placed within handle 201 exhibiting snug fit or closer tolerance with the inner diameter of hollow handle 201. In this manner, contact face 216 could be realized by machining it into the face of a support plate 209. In such a case, support plate 209 would be made of a conductive material such as copper steel, brass, or the like, and could be either a perforated plate or fritted material as described above.

In an additional alternative embodiment (not illustrated), the end of handle 201 could be open, with separate conduits for a wire bearing the rf energy and the inert gas running up the bore of handle 201, terminating in connectors supported by a solid support plate 209. In such an embodiment, support plate 209 would be rigidly fixed within the bore of handle 201. Fixture of support plate 209 in such a case could be by any means known in the art such as shrink fit, welding, adhesives, brazing, or using mechanical fastening means, such as threading of the inner walls of hollow handle 201 and the outer edge of support plate 209, machining a relief into the inner wall of hollow handle 201 into which support plate 209 fits and then securing it in place with screws, bolts, snap rings, or the like. Wire and gas conduits could as well be run along the outside of handle 201 and connected with mechanical feed-through devices, such as are well known in the art, to effect connection between the source of rf energy and convey gas to the electrode. In such a case, electrical connection to contact 216 could be made through a conductive support plate 209, or via a feed-through to a contact 216 mounted on a non-conducting support plate 209.

Nozzle assembly 202 consists of a tapered section extending from threaded portion 205 to the tip through which electrode 212 protrudes. The tapered section may be of any convenient length, and typically is in the range of 3 cm to 45 cm. Short nozzles are generally used for conventional surgery work while long nozzles are generally employed in endoscopic or laproscopic surgical procedures or when creating or working within a cavity or pocket.

Electrode 212 is rigidly supported within nozzle assembly 202 by plenum 213 on the tip end of the nozzle assembly and by support plate 214 on the threaded end of nozzle assembly 202. Support plate 214 is perforated to permit gas emerging from handle 201 to pass into tip assembly 202 when it is assembled to handle 201. Alternatively, support plate 214 may be porous in the same manner disclosed above for support plate 209.

Plenum 213 is positioned at the tip end of nozzle assembly 202. It is a perforated disk fixed within the bore of nozzle assembly 202 that supports surgical end of electrode 212, the electrode passing thorough a center bore in plenum 213 and protruding from the end of nozzle assembly 202. Plenum 213 is further illustrated in FIG. 3.

Figure 3:
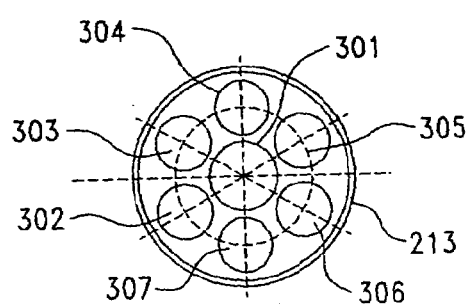
FIG. 3: Elevation View of a Plenum According to the Present Invention.

With reference to FIG. 3, in the preferred embodiment, Plenum 213 is a disk about 2 mm thick and of sufficient diameter to form a press fit with the inner diameter of nozzle assembly 201. Plenum 213 contains through bored hole 301 centered on the flat face of the plenum. Through bored hole 301 is of sufficient diameter to form a snug or press fit with the outside diameter of electrode 212. Additionally, plenum 213 has through bored about its radius holes 302–307 which serve to form a series of radial columns of gas that blanket electrode 212 when the assembled instrument is in operation. The diameter and placement of these holes is determined by the extent of electrode 212 tip beyond the end of nozzle assembly 202. Generally, as the electrode extends further from the end of the nozzle the holes are arranged to give a column of gas that projects further from the end of the nozzle. Placement of plenum 212 at the tip of nozzle assembly 202 serves to concentrate the gas flow at the surgical site, enhancing hemostasis during surgery and removing fluid from the incision site.

Figure 4:
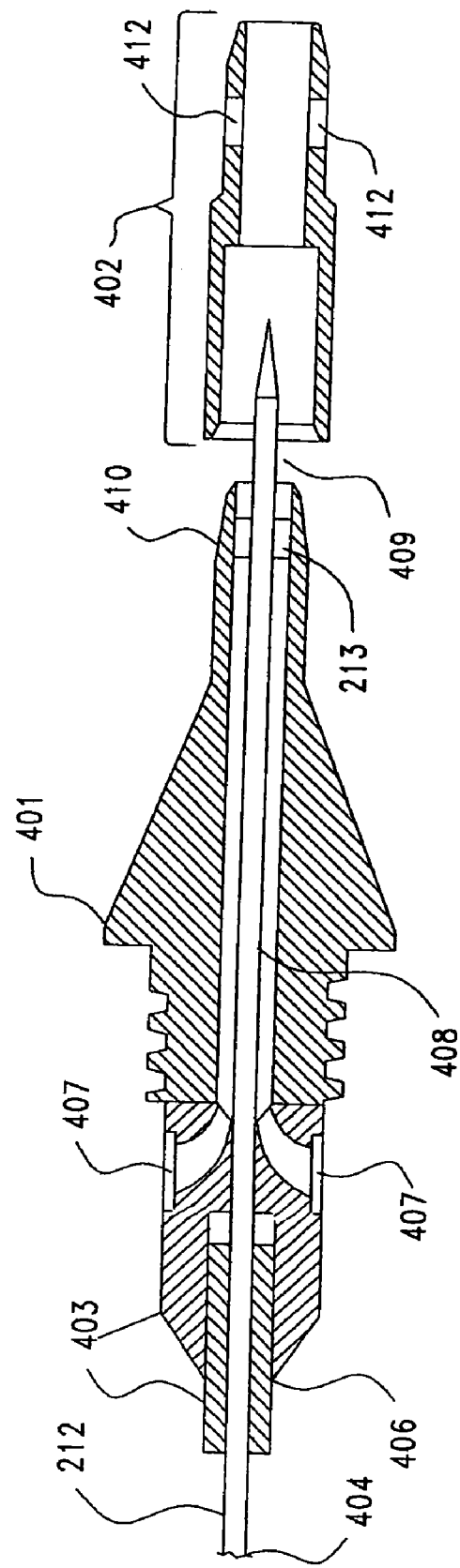
FIG. 4: Cutaway Plan View of the Present Invention Electrode Assembly and Shroud.

FIG. 4 contains further detail of nozzle assembly 202. With reference to FIG. 4, nozzle assembly 202 is comprised of electrode 212, electrode holder 403, nozzle 401, and shroud 402. Nozzle 401 is shown with plenum 213 installed in the tip. Nozzle 401, plenum 213, electrode 212, electrode holder 403 when assembled are the functional equivalent of nozzle assembly 202 of FIG. 2.

Nozzle 401 contains through-bored channel 408. Channel 408 is of sufficient diameter that when electrode 212 is placed in the center of the bore, sufficient clearance exists between the electrode and the inner walls of the nozzle channel 408 that a gas flow can be readily maintained at the tip of the nozzle. One end of nozzle 401 is provided with suitable means to connect the nozzle to a handle (disclosed above) and a shank portion that extends beyond the threaded portion into the handle. The shank portion has slots 407 machined into it. The slots are through bored and intersect through bore channel 408. In this manner, a gas stream emerging from support plate 209 in the handle is directed along the shank portion of the electrode assembly through slots 407 and thereby into channel 408 within nozzle 401 and thence out tip 409 of the nozzle.

Contact end 404 of electrode 212 may be of any shape suitable to be received by, with reference to FIG. 2, support plate 214. In the preferred embodiment, support plate 214 has a recess (not shown) machined into it, centered in the face obverse contact 215. The recess has a diameter sufficient to permit a snug or press fit between electrode 212 and the recess. The bottom of the recess is rounded to compliment the rounded contact end 404 of electrode 212, such that when electrode 212 is pressed into the recess intimate contact is made between the recess bottom and contact end 404.

Electrode 212 is prevented from sliding out of nozzle 401 when nozzle assembly 202 is attached to handle 201 by electrode holder 403. Electrode holder 403 may be fastened to electrode 212 using an adhesive agent or a weld or braze joint between electrode holder 403 and electrode 212, such as is well known in the art of fastening materials. Alternatively, the shank of electrode 212 may be tapered, decreasing in diameter in the direction of working tip 405 of electrode 212. The inner diameter of electrode holder 403 may be tapered in the opposite direction such that as electrode 212 is inserted further into electrode holder 403 it is wedged within holder 403. Electrode holder 403 in turn displays a snug fit between recess 406 of nozzle 401 and its outer diameter. When the assembled electrode and electrode holder is pressed into the recess of nozzle 401, the assembly stops against the bottom of recess 406, and electrode 212 is thereby firmly retained in nozzle 401. Other alternatives for securing electrode 212, such as a conventional collet assembly and the like well known in the art, may be likewise employed equally effectively.

After nozzle 401 is secured to handle 201 with electrode 212 secured within a nozzle assembly thereby, shroud 402 is placed in position on end 409 of nozzle 401. Shroud 402 is a tube having a tapered inside bore 410 that compliments the taper of the outer surface 411 of nozzle 401. In use, shroud 402 is pressed onto nozzle 401. The close tolerance friction fit between the two pieces is such that shroud 402 is retained on nozzle 401 until deliberately pried off of nozzle 401. Shroud 402 is shaped such that when place on nozzle 401, the internal diameter of the open end of shroud 402 is 3 times the size of the nominal diameter of electrode 404. Additionally, the length of shroud 402 is such that when in place on the end of nozzle 401, the tip of electrode 212 resides between 1 millimeter recessed inside the end of shroud 402 and 15 millimeter protruding from shroud 402. As is indicated in the prior art, a "gas beam" effect for cutting is available if the electrode is recessed significantly within the shroud, but gas enhanced dissection is enabled when the electrode protrudes from the shroud a distance of from about 7 mm to a distance of about 15 mm.

Figures 5, 6:
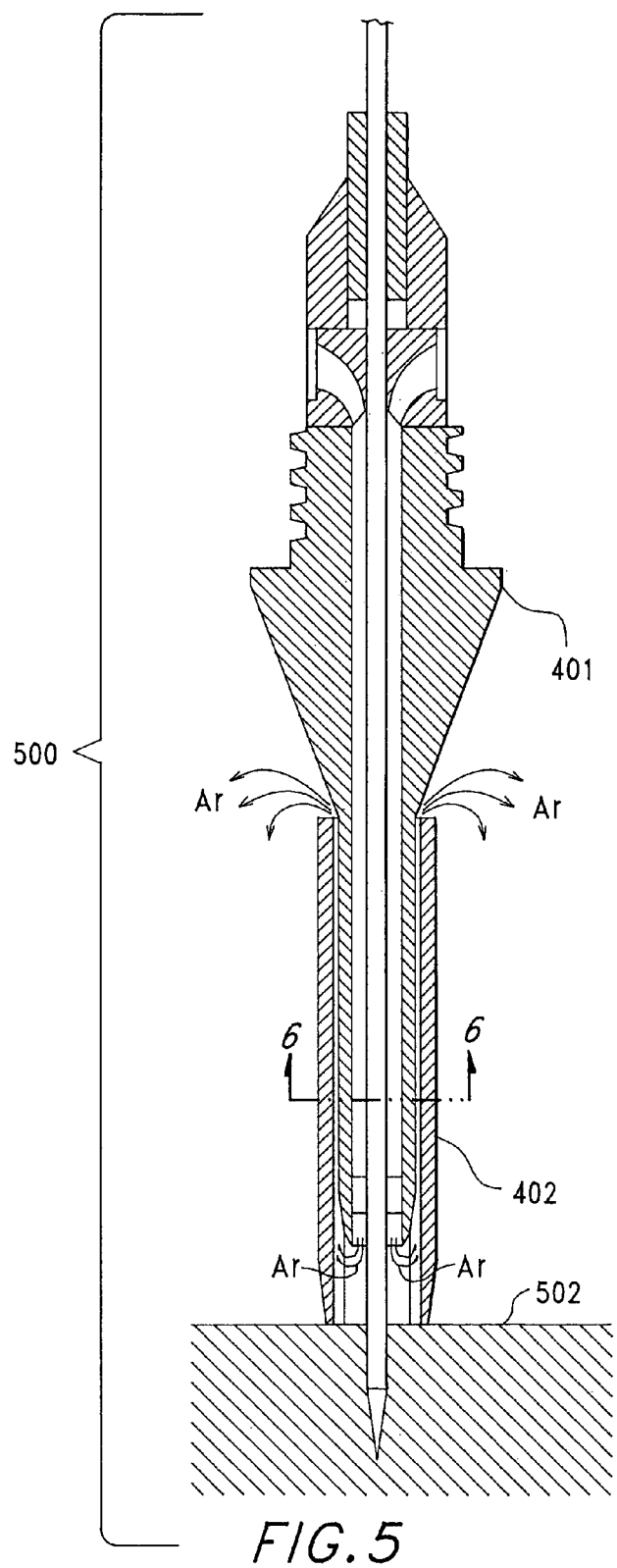
FIG. 5: Elevation View of the Present Invention Shroud.
FIG. 6: Cutaway view taken along line 6—6 of FIG. 5.

One additional feature of shroud 402 is the plethora of gas pressure relief openings 412 about the circumference of shroud 402 that permit gas to escape from shroud 402 through such openings. The gas pressure relief openings may be in the form of holes of any shape completely penetrating the walls of shroud 402 which extend from the open end of installed shroud 402 to a point any distance along the sidewall of shroud 402. Gas pressure relief openings 412 in the form of holes may be of any shape, number, and placement about the circumference of shroud 402 so long as sufficient open area exists between the openings such that in use, when the open end of shroud 402 is pressed against tissue, insufficient gas pressure is built up within the shroud to cause a gas embolism in the contacted tissue. Alternatively, the gas pressure relief openings may be in the form of slots milled longitudinally (parallel to the bore axis) in the inside wall of shroud 402 extending the entire length of the shroud. With reference to FIG. 6, these slots 501 form a series of void spaces between shroud 402 and nozzle 401. In this manner, when the tip of shroud 402 is pressed against tissue bed 502, gas pressure generated between tissue bed 502 and electro-surgical instrument 500 is relieved by permitting the gas to pass through void spaces 501. It is preferred that a cumulative open area for all openings 412 exceeds the minimum required to prevent gas embolism, in the event that one or more should become blocked by material or contact with tissue during a procedure, thus allowing for a margin of safety. It is also preferable that openings 412 be distributed evenly about the perimeter of shroud 402. This distribution insures that the operation of openings 412 won't be impaired should one portion of the side of shroud 402 inadvertently contact tissues during use, blocking one or more openings 412.

Although the components of handle 201, the non-conducting parts of nozzle assembly 202, and shroud 402 may be made of any type of plastic, ceramic, or glass material well known in materials science, acetyl plastic is the preferred material of construction. As well, any type of conducting material may serve from which to fashion electrode 212, but preferred are titanium and/or refractory metals, more preferred are refractory metals that are stiff with high hardness, with an electrode made of primarily titanium and/or tungsten metal being most preferred. The preferred electrode materials have mechanical properties such that they are sufficiently robust that an instrument having a small cross-section is sufficiently strong enough to be used to mechanically dissect tissues. Additionally, the preferred electrode materials have a refractory property such that small cross-section features of such materials resist melting under the energy throughput experienced in an electrosurgical procedure. And finally, the preferred electrode materials are capable of being fashioned into an electrode that can be tapered to a tip with a cross-sectional area that is less than 99% of the diameter of the nominal electrode diameter. In general, the ideal electrode tip has a diameter of 1 atom across. This idealized tip has not yet been realized, but through techniques such as electro-polishing and directional grinding to enhance the tip taper, tips of very small cross-sectional area can be realized.

It will be apparent to one skilled in the art that nozzle 401 may be made to any length, and may even be made of flexible material, with electrode 212 being soldered to the end of a flexible, conductive material, such as a stainless steel cannula and the like, such as are well known in the art.

The following example is illustrative of the present invention. A hollow handle 12 cm long and 1.5 cm diameter was fitted at one end with a compression fitting for connecting a gas supply line and a socket for connecting an rf supply line. The other end of the handle is threaded with a coarse internal thread into which the nozzle assemble can be fitted by means of a matching external thread. A nozzle assembly with a thread at one end corresponding to that of the handle piece above and a tapered nozzle at the other was machined from acetyl plastic stock obtained from [supplier]. The finished nozzle was 7.1 cm long and 1.4 cm in diameter, with an internal bore of 3 mm. Into this nozzle was fitted a 1 mm nominal diameter tungsten electrode 7.1 mm long obtained from Victorian Welding Supplies. It was secured in the nozzle by [means for securing the electrode]. One end of the electrode was tapered over 10 mm to a tip with a diameter of less than 10 microns. This nozzle assembly was fastened to the handle using the inside and outside threaded portions described above and the open end of the assembled instrument was fitted with a shroud made of the same acetyl plastic disclosed above. This shroud contained six longitudinal slots machined at intervals of 60° about the inside diameter interior wall of the shroud openings giving a cross-sectional open area equal in area to the holes through the plenum. When pressed onto the end of the nozzle assembly, this internally slotted shroud required the application of a force in excess of 0.5 kg to remove it. When assembled, the tip of the electrode protruded from the end of the shroud by 10 mm.

The assembled instrument was connected to a ConMed ABC Argon Beam Coagulator. Argon was passed through the instrument at 6 liters/minute (lpm) and a power setting of 45 watts/modulated current was used to perform abdominoplasty. It was found that the instrument described above permitted the use of a lower energy setting and provided a surgical outcome that was a marked improvement over instruments not using the combination of a sharp needle electrode and a gas shroud. It was noted that when compared to prior art instruments the present invention provided faster hemostatis, cleaner dissection, reduced the smoke plume and odor normally associated with electrosurgical procedures to a level that required no additional equipment to manage of either, produced wounds that exhibited less tissue damage and charring. Additionally, the present invention permitted executing surgical procedures faster, reducing the time required to execute the procedure. The present invention provided wounds that exhibited reduced postoperative drainage and the patient exhibited reduced post-operative bruising. It was also found that the instrument could contact tissue without producing a gas embolism or other tissue damage typical of such electrode contact. Additionally, the present invention could be utilized with less eschar buildup on the electrode tip, reducing the time required to carry out surgical procedures.

It will be appreciated to one skilled in the art that, although less convenient from a sterilization and disposal standpoint, the above disclosed nozzle and shroud may be a single piece rather than two pieces and still be within the scope of the claimed invention. Additionally, the shroud could be modified by placing a flexible, spring like, or elastomeric material over the openings such that it functions like a pressure relief valve, while permitting a lower flow rate of blanketing gas and still it would be within the scope of the present invention.

As well it will be appreciated that a sharp needle tip electrode is but one of many electrode shapes that could benefit from the application of the present invention shroud. Examples of such electrodes are curved tips, loops, hooks, and blades, and the like such as are well known in the art. As well the present invention may be utilized with insulated or uninsulated electrodes as well as partially insulated electrodes, all of which are also known in the art. Finally, the present invention is equally useful when practiced with electrodes which have been adapted to laproscopic work, such as those which employ a sliding sleeve to afford protection to the tissues and the electrode during insertion into the laproscopic incision and the like, such as are also well known in the art.

Although the present invention has been described with reference to preferred embodiments, numerous modifications and variations can be made and still the result will come within the scope of the invention. No limitation with respect to the specific embodiments disclosed herein is intended or should be inferred.

I claim:

1. In an instrument for carrying out an electrosurgical procedure on tissue, said instrument comprising a handle, a gas source, a nozzle for directing the gas source, an electrode connected to an electrosurgical generator, and a sleeve at least partially shielding said electrode, the improvement comprising:
   a shroud isolating a portion of the active end of an electrode; and
   openings in the side wall of the shroud to dissipate gas upon flesh contact when said electrode active end and said shroud are buried in tissue.

2. The improved electro-surgical instrument of claim 1, wherein said shroud side wall openings comprise a series of slots fashioned about the inside diameter of the shroud internal wall, not penetrating said shroud wall, and running longitudinally the length of said shroud, whereby gas may vent through said slots and out into the ambient when the tip of said electro-surgical instrument is pressed against tissue present at a surgical site.

3. The improved electro-surgical instrument of claim 1, wherein said shroud sidewall openings comprise a series of holes fashioned about the diameter of the shroud and completely penetrating the wall of said shroud.

4. The improved electro-surgical instrument of claim 1 wherein said shroud is slidably mounted on said electrosurgical apparatus.

5. The improved electro-surgical instrument of claim 1, wherein the portion of the active end of the electrode not isolated by said shroud is between about 7 mm and about 20 mm.

6. In an instrument for carrying out an electrosurgical procedure on tissue, said instrument comprising a handle, a gas source, a nozzle for directing the gas source, an electrode connected to an electrosurgical generator, and a sleeve at least partially shielding said electrode, the improvement comprising:

a shroud having a press fit over said nozzle for directing the gas source such that when placed over said tip, said shroud isolates a portion of the active end of an electrode; and slots in the inner wall of the shroud whereby an open path is provided to vent gas upon flesh contact when said electrode active end and said shroud are buried in tissue.

* * * * *